United States Patent
Blagoev et al.

(10) Patent No.: US 9,476,888 B2
(45) Date of Patent: Oct. 25, 2016

(54) METHOD AND ANTIBODIES FOR THE IDENTIFICATION OF UBIQUITINATED PROTEINS AND SITES OF UBIQUITINATION

(75) Inventors: Blagoy Blagoev, Odense SOE (DK); Jens Vanselow, Odense M (DK); Vyacheslav Akimov, Odense S (DK); Mogens Nielsen, Odense M (DK)

(73) Assignee: SYDDANSK UNIVERSITET, Odense M (DK)

( * ) Notice: Subject to any disclaimer, the term of this patent is extended or adjusted under 35 U.S.C. 154(b) by 106 days.

(21) Appl. No.: 14/237,626

(22) PCT Filed: Jul. 31, 2012

(86) PCT No.: PCT/DK2012/050282
§ 371 (c)(1),
(2), (4) Date: May 13, 2014

(87) PCT Pub. No.: WO2013/020557
PCT Pub. Date: Feb. 14, 2013

(65) Prior Publication Data
US 2015/0309046 A1    Oct. 29, 2015

Related U.S. Application Data

(60) Provisional application No. 61/521,016, filed on Aug. 8, 2011.

(30) Foreign Application Priority Data

Aug. 8, 2011  (DK) ................................ 2011 00597

(51) Int. Cl.
G01N 33/68    (2006.01)
C07K 7/08    (2006.01)
C07K 16/18    (2006.01)

(52) U.S. Cl.
CPC ............ *G01N 33/6854* (2013.01); *C07K 7/08* (2013.01); *C07K 16/18* (2013.01); *G01N 33/6842* (2013.01); *C07K 2317/34* (2013.01); *G01N 2440/36* (2013.01)

(58) Field of Classification Search
CPC .... C07K 7/08; C07K 16/18; C07K 2317/34; G01N 33/577; G01N 33/6818; G01N 33/6854; G01N 33/6872; G01N 2440/36; G01N 2800/7057
See application file for complete search history.

(56) References Cited

U.S. PATENT DOCUMENTS

| | | | |
|---|---|---|---|
| 2006/0148093 A1* | 7/2006 | Gygi | ........................ C07K 7/08 436/173 |
| 2009/0317409 A1 | 12/2009 | Xu et al. | |
| 2010/0331200 A1 | 12/2010 | Gordon et al. | |

FOREIGN PATENT DOCUMENTS

WO    2007/123708    * 11/2007

OTHER PUBLICATIONS

Matsumoto et al., 2005. Large-scale analysis of the human ubiquitin-related proteome. Proteomics 5: 4145-4151.*
Fujimoro et al., 1994. Production and characterization of monoclonal antibodies specific to multi-ubiquitin chains of polyubiquitinated proteins. FEBS Letters 349: 173-180.*
Hochstrasser, "Origin and Function of Ubiquitin-like Proteins," Nature, vol. 458, (Mar. 26, 2009), pp. 422-429.
Van Der Veen et al. "Ubiquitin-Like Proteins," Annu. Rev Biochem. (2012), pp. 323-357.
Deribe et at "Post-translational modifications in signal integration," nature structural & molecular biology, vol. 17, No. 6, (Jun. 2010), pp. 666-672.

* cited by examiner

*Primary Examiner* — Jacob Cheu
(74) *Attorney, Agent, or Firm* — Merchant & Gould P.C.

(57) ABSTRACT

There is provided antibodies, epitopes and methods for detecting ubiquitinated polypeptides and ubiquitination sites in proteins. The antibodies recognize a fragment of ubiquitin that is created after samples are treated with the proteoloytical enzyme LysC (or LysN).

5 Claims, No Drawings

```
                           SEQUENCE LISTING

<160> NUMBER OF SEQ ID NOS: 7

<210> SEQ ID NO 1
<211> LENGTH: 13
<212> TYPE: PRT
<213> ORGANISM: Homo sapiens

<400> SEQUENCE: 1

Glu Ser Thr Leu His Leu Val Leu Arg Leu Arg Gly Gly
1               5                   10

<210> SEQ ID NO 2
<211> LENGTH: 16
<212> TYPE: PRT
<213> ORGANISM: Homo sapiens

<400> SEQUENCE: 2

Ile Leu Gly Gly Ser Val Leu His Leu Val Leu Ala Leu Arg Gly Gly
1               5                   10                  15

<210> SEQ ID NO 3
<211> LENGTH: 14
<212> TYPE: PRT
<213> ORGANISM: Homo sapiens

<400> SEQUENCE: 3

Pro Leu Ser Thr Val Phe Met Asn Leu Arg Leu Arg Gly Gly
1               5                   10

<210> SEQ ID NO 4
<211> LENGTH: 17
<212> TYPE: PRT
<213> ORGANISM: Homo sapiens

<400> SEQUENCE: 4
```

```
Lys Ile Leu Gly Gly Ser Val Leu His Leu Val Leu Ala Leu Arg Gly
1               5                   10                  15

Gly

<210> SEQ ID NO 5
<211> LENGTH: 15
<212> TYPE: PRT
<213> ORGANISM: Homo sapiens

<400> SEQUENCE: 5

Lys Pro Leu Ser Thr Val Phe Met Asn Leu Arg Leu Arg Gly Gly
1               5                   10                  15

<210> SEQ ID NO 6
<211> LENGTH: 14
<212> TYPE: PRT
<213> ORGANISM: Homo sapiens

<400> SEQUENCE: 6

Lys Glu Ser Thr Leu His Leu Val Leu Arg Leu Arg Gly Gly
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic Protein

<400> SEQUENCE: 7

Glu Ser Thr Leu His Leu Val Leu Arg Leu Arg Gly Gly Cys
1               5                   10
```

US 9,476,888 B2

METHOD AND ANTIBODIES FOR THE IDENTIFICATION OF UBIQUITINATED PROTEINS AND SITES OF UBIQUITINATION

This application is a National Stage Application of PCT/DK2012/050282, filed 31 Jul. 2012, which claims benefit of Serial No. PA 2011 00597, filed 8 Aug. 2011 in Denmark, and claims benefit of U.S. Provisional Application Ser. No. 61/521,016, filed 8 Aug. 2011, and which applications are incorporated herein by reference. To the extent appropriate, a claim of priority is made to each of the above disclosed applications.

FIELD OF THE INVENTION

The present invention provides antibodies, epitopes and methods for detecting ubiquitinated polypeptides and ubiquitination sites in proteins.

BACKGROUND OF THE INVENTION

Protein ubiquitination is a widespread reversible post-translational modification that is used by eukaryotic cells as a major regulatory mechanism to alter protein stability, localization, conformation and activity of the modified substrates. Ubiquitin is a highly conserved 76 amino acid protein and conjugation of ubiquitin to target proteins requires a series of enzymatic reactions (Pickart, 2001): After activation of ubiquitin through the formation of a thioester bond between its C-terminal glycine and the active site cysteine of the ubiquitin activating protein E1, it is transferred by subsequent trans-thiolation reactions to a cysteine residue on a ubiquitin conjugating enzyme, E2. Finally, a substrate specifity determining ubiquitin ligase (E3) transfers ubiquitin bound to E2 to a specific polypeptide target, forming an isopeptide bond between the C-terminal glycine of ubiquitin and the $\epsilon$-amino group of a lysine present in the target. Ubiquitin itself can also undergo ubiquitination on any of its seven lysine residues resulting in formation of distinct poly-ubiquitin chains (Komander, 2009). Depending on the number and type of ubiquitin moieties attached, a protein can be mono-ubiquitinated, multiple mono-ubiquitinated at different lysines and poly-ubiquitinated. This heterogeneity plays a critical role in molecular recognition of the modified proteins by numerous types of ubiquitin binding proteins (Hicke, 2005). In addition, the size and type of ubiquitin conjugates serve as a specific code for determination of the fate of tagged proteins. For example, modification by Lysine-48 poly-ubiquitin chains directs proteins mainly for degradation by the 26S proteasome, whereas mono-ubiquitination and Lysine-63 type poly-ubiquitination have been associated with regulation of several cellular processes including signal transduction, endocytosis, chromatin rearrangement and DNA repair (Haglund, 2005; Mailand, 2007; Messick, 2009; Pandita, 2009).

Due to the large dynamic range of protein expression and a generally low stoichiometry of ubiquitination on proteins, it is challenging to identify the ubiquitinated proteins and ubiquitination sites on these proteins. As a consequence of these challenges there are only a limited number of reports investigating protein ubiquitination on a proteomic scale. Mass spectrometric approaches have mainly been limited to affinity enrichment of ubiquitinated proteins using overexpressed tagged ubiquitin (Gururaja, 2003; Peng, 2003; Danielsen, 2011; Argenzio, 2011) or poorly-working antibodies raised against ubiquitin (Argenzio, 2011; Matsumoto, 2005; Vasilescu, 2005). Another strategy to enrich directly modified peptides from ubiquitinated targets using antibodies against the remnant diglycine of ubiquitin on lysine residues after tryptic digestion has been recently developed.

Because of the complex nature of ubiquitination, its heterogeneity and the lack of suitable procedures there is a need for new strategies to study ubiquitination on a proteomic scale.

Ubiquitin has been implicated in a number of cellular processes including: signal transduction, cell-cycle progression, receptor-mediated endocytosis, transcription, organelle biogenesis, spermatogenesis, response to cell stress, DNA repair, differentiation, programmed cell death, and immune responses (e.g., inflammation). Ubiquitin also has been implicated in the biogenesis of ribosomes, nucleosomes, peroxisomes and myofibrils. Thus, ubiquitin can function both as signal for polypeptide degradation and as a chaperone for promoting the formation of organelles.

Deregulation of ubiquitination has been implicated in the pathogenesis of many different diseases. For example, abnormal accumulations of ubiquitinated species are found in patients with neurodegenerative diseases such as Alzheimer's as well as in patients with cell proliferative diseases, such as cancer.

While the importance of its biological role is well appreciated, the ubiquitin pathway is inherently difficult to study. Generally, studies of ubiquitination have focused on particular polypeptides. For example, site-directed mutagenesis has been used to evaluate critical amino acids which form the "destruction boxes" or "D-boxes" of cyclin, sites which are rapidly poly-ubiquitinated when cyclin is triggered for degradation. Moreover, the ubiquitin-proteosome system is the principal mechanism for the turnover of short-lived polypeptides, including regulatory polypeptides.

Although mass spectrometry offers a powerful tool for identifying ubiquitin substrates, a number of unresolved issues remain. Despite many advances, MS data is inherently biased towards more abundant substrates. The effects of ubiquitin epitope tags used to enrich ubiquitinated proteins remain incompletely understood, including whether purification biases exist and whether ubiquitin pathway enzymes utilize tagged and wild-type ubiquitin with equal efficiency.

Unfortunately, not many ubiquitination sites have currently been identified in mammalian cells. Therefore, information on how to manipulate ubiquitination and modulate some of the processes involving ubiquitination is lacking. Furthermore, methods to profile ubiquitination in cells and tissues are insufficient, and would require additional tools that allow for the simple, sensitive, specific, and rapid detection of ubiquitination sites in biological samples.

It is an object of the present invention to provide antibodies and a detection strategy to enable the sensitive, specific, and rapid detection of ubiquitination sites in biological samples.

SUMMARY OF THE INVENTION

The present invention is based on polyclonal and monoclonal antibodies that facilitate identification of ubiquitinated proteins and their direct ubiquitination site in cells and tissues. These antibodies recognize a fragment of ubiquitin that is created after samples (comprising proteins that are ubiquitinated, either as pure proteins or in a mixture of proteins, such as a cell lysate) are treated with the proteoloytical enzyme LysC (or LysN). The epitope that is recognized by the antibodies has the sequence ESTLHLV-LRLRGG (SEQ ID NO 1), said antibodies being able to specifically distinguish between ubiquitin and ubiquitin-like modified peptides. When LysN is used the epitope sequence is extended with a lysine residue in the N-terminal end to KESTLHLVLRLRGG (SEQ ID NO 6).

The antibodies of the present invention have been successfully used for immunopurification of ubiquitinated peptides obtained from mammalian cells and many ubiquitination sites have been identified by mass spectrometry of the immunoprecipitated peptides. Use of these antibodies to identify and isolate ubiquitinated peptides from a complex peptide mixture has many applications. Identification of ubiquitination sites will expand our understanding of the biological role of ubiquitination, will permit the discovery of substrates for specific protein ubiquitination ligases, and will enable the detection of substrates in ubiquitination-related diseases.

Therefore, one aspect of the invention is the isolated epitope having the sequence ESTLHLVLRLRGG (SEQ ID NO 1).

Another aspect of the invention is an antibody (hereinafter the antibody of the present invention) that specifically binds to the epitope having the sequence ESTLHLVLRLRGG (SEQ ID NO 1). The antibody can be a monoclonal or polyclonal antibody.

Another aspect of the invention is a method of detecting a ubiquitinated site in a test protein or a mixture of test proteins that comprises
(i) cleaving a test protein or a mixture of test proteins with a protease, such as LysC, that cleaves ubiquitin to form a mixture of cleavage peptides;
(ii) contacting the cleavage peptides with an antibody of the present invention; and
(iii) identifying the peptide(s) that bind to the antibody thereby detecting and identifying a ubiquitinated site in a test protein or a mixture of test proteins.

In this strategy, LysC is used to cleave proteins derived e.g. from cell lysate. LysC generates cleavage peptides from the proteins present in the cell lysate, dependent on the presence of (not modified) K residues in the protein sequence(s). This is an important step for generating the epitope required for the antibody to enrich peptides containing/being modified with this ubiquitin remnant.

After enriching LysC peptides carrying the ubiquitin remnant, an (optional) cleavage with other proteases, e.g. with trypsin, may be performed in order to facilitate peptide analysis by mass spectrometry. In this case, a modified LysC peptide (with the ubiquitin remnant) further digested with e.g. trypsin gives rise to one peptide containing a diglycine (GG) remnant as modification of lysine residues and—dependent on the sequence of the modified peptide (i.e. the presence of other K or R residues) other shorter peptides not containing a modified lysine residue.

MS analysis and database searching can then be used to detect and identify the GG containing peptides and the position of the GG-modification inside the protein from which the peptide was derived.

The methods and antibodies described herein can be used to identify ubiquitination sites, patterns and profiles in a variety of samples. For example, the sample to be evaluated can be a body fluid, tissue sample, cell lysate, fractionated cellular material, cellular extract, cell culture supernatant, or cultured cells. Similarly, a variety of body fluids can be evaluated using the methods described herein. For example, the body fluid can be saliva, mucous, sweat, whole blood, serum, urine, amniotic fluid, genital fluid, fecal material, marrow, plasma, spinal fluid, pericardial fluid, gastric fluid, abdominal fluid, peritoneal fluid, pleural fluid, synovial fluid, cyst fluid, cerebrospinal fluid, lung lavage fluid, lymphatic fluid, tears, prostatitc fluid, tissue extract, or glandular secretion. In some embodiments, the sample is obtained from a mammal fed a diet containing an isotopically-labeled amino acid.

For example, when the sample is a selected cell or tissue type, the method can be adapted to include identifying substantially all prominently ubiquitinated proteins in the cell or tissue type to yield a ubiquitination profile of proteins from the cell or tissue type. The method can further include comparing the ubiquitination profile of proteins from a diseased cell or tissue type with a ubiquitination profile of proteins from a normal cell or tissue type. In addition, the method can further include comparing the ubiquitination profile of proteins from the cell or tissue type with a ubiquitination profile of proteins from the cell or tissue type after treatment or exposure of the selected cells or tissues to a drug or test agent. The method can further include comparing the ubiquitination profile of proteins from the cell or tissue type with a ubiquitination profile of proteins from cells with a mutation (e.g., a deletion or insertion) or amplification of a gene encoding a ubiquitin ligase, a ubiquitin conjugating enzyme or a ubiquitin activating enzyme. For example, the mutation can substantially eliminate expression or function of an E3 ubiquitin ligase, an E2 ubiquitin conjugating enzyme or an E1 ubiquitin activating enzymes. The amplification of a gene encoding a ubiquitin ligase, a ubiquitin conjugating enzyme or a ubiquitin activating enzyme can lead to overexpression of the ubiquitin ligase, the ubiquitin conjugating enzyme or the ubiquitin activating enzyme.

Another aspect of the invention is a method of generating an antibody that comprises administering to a mammal or other suitable organism an effective amount of an antigen comprising the epitope of the present invention to generate an immune response against the epitope, to thereby generate an antibody of the present invention.

Additional Embodiments

In addition to ubiquitin itself, several ubiquitin-like modifiers exist, including NEDD8 or ISG15, which are—like ubiquitin—conjugated to target proteins by a similar conjugation cascade and fulfill a similar range of functions as ubiquitin. To specifically distinguish between ubiquitin and ubiquitin-like modifiers, the attachment of e.g. NEDD8 or ISG15 to target proteins is termed NEDDylation or ISGylation, respectively.

Embodiment A (NEDD8)

1a. An antibody that specifically binds to an epitope having the sequence ILGGSVLHLVLALRGG (SEQ ID NO 2).

2a. The antibody of embodiment 1a, wherein the antibody is a polyclonal antibody.

3a. The antibody of embodiment 1a, wherein the antibody is a monoclonal antibody.

4a. An isolated epitope having the sequence ILGGSVLHLVLALRGG (SEQ ID NO 2).

5a. A method of detecting a NEDDylated site in a test protein or a mixture of test proteins that comprises
(i) cleaving a test protein or a mixture of test proteins with a protease, such as LysC, that cleaves NEDD8 to form a mixture of cleavage peptides;
(ii) contacting the cleavage peptides with an antibody that specifically binds to an epitope having the sequence ILGGSVLHLVLALRGG (SEQ ID NO 2); and (iii) analysing the peptide(s) that bind to the antibody thereby detecting and identifying a NEDDylated site in a test protein or a mixture of test proteins.

6a. The method of embodiment 5a, wherein the protease that cleaves NEDD8 also cleaves protein(s) in the sample.

7a. The method of any one of the embodiments 5a-6a, wherein the protease that cleaves NEDD8 is LysC or LysN. When LysN is used the epitope sequence is extended with a lysine residue in the N-terminal end; KILGGSVLHLVLA-LRGG (SEQ ID NO 4)

8a. The method of any one of the embodiments 5a-7a further comprising sequencing the cleavage peptide to which the antibody binds to thereby determine the amino acids sequence of the cleavage peptide.

9a. The method of embodiment 8a, wherein the cleavage peptide is further hydrolysed before sequencing/identification, preferably by a protease, even more preferably by trypsin.

10a. The method of embodiment 9a, wherein the sequencing/identification is performed by a method comprising mass spectrometry.

11a. The method of embodiment 10a further comprising identifying the NEDDylated site in the cleavage peptide.

Embodiment B (ISG15)

1b. An antibody that specifically binds to an epitope having the sequence PLSTVFMNLRLRGG (SEQ ID NO 3).

2b. The antibody of embodiment 1b, wherein the antibody is a polyclonal antibody.

3b. The antibody of embodiment 1b, wherein the antibody is a monoclonal antibody.

4b. An isolated epitope having the sequence PLSTVFMNLRLRGG (SEQ ID NO 3).

5b. A method of detecting a ISGylated site in a test protein or a mixture of test proteins that comprises
(i) cleaving a test protein or a mixture of test proteins with a protease, such as LysC, that cleaves ISG15 to form a mixture of cleavage peptides;
(ii) contacting the cleavage peptides with an antibody that specifically binds to an epitope having the sequence PLSTVFMNLRLRGG (SEQ ID NO 3); and
(iii) analysing the peptide(s) that bind to the antibody thereby detecting and identifying a ISGylated site in a test protein or a mixture of test proteins.

6b. The method of embodiment 5b, wherein the protease that cleaves ISG15 also cleaves protein(s) in the sample.

7b. The method of any one of the embodiments 5b-6b, wherein the protease that cleaves ISG15 is LysC or LysN. When LysN is used the epitope sequence is extended with a lysine residue in the N-terminal end; KPLSTVFMNLRL-RGG (SEQ ID NO 5)

8b. The method of any one of the embodiments 5b-7b further comprising sequencing the cleavage peptide to which the antibody binds to thereby determine the amino acids sequence of the cleavage peptide.

9b. The method of embodiment 8b, wherein the cleavage peptide is further hydrolysed before sequencing/identification, preferably by a protease, even more preferably by trypsin.

10b. The method of embodiment 9b, wherein the sequencing/identification is performed by a method comprising mass spectrometry.

11b. The method of embodiment 10b further comprising identifying the ISGylated site in the cleavage peptide.

Embodiment C

As mentioned above the epitope sequence (SEQ ID NO 1) is extended with a lysine residue in the N-terminal end when LysN is used. Accordingly this embodiment is simply defined by the claimed subject-matter except that the epitope has the sequence KESTLHLVLRLRGG (SEQ ID NO 6).

DETAILED DESCRIPTION OF THE INVENTION

Prior to describing various embodiments of the current invention, the following definitions are provided:

As used herein the term "peptide" or "polypeptide" refers to a polymer formed from the linking, in a defined order, of preferably, α-amino acids, D-, L-amino acids, and combinations thereof. The link between one amino acid residue and the next is referred to as an amide bond or a peptide bond. Proteins are polypeptide molecules (or having multiple polypeptide subunits). The distinction is that peptides are preferably short and polypeptides/proteins are preferably longer amino acid chains. The term "protein" is intended to also encompass derivatized molecules such as glycoproteins and lipoproteins as well as lower molecular weight polypeptides.

As used herein, the term "ubiquitinated polypeptide" refers to a polypeptide bound to ubiquitin, a ubiquitin-like protein (e.g. NEDD8 or ISG15) or a portion thereof. Preferably, ubiquitination is the formation of an isopeptide bond between the C-terminal glycine of ubiquitin (or ubiquitin-like protein) and the ε-amino group of a lysine present in the target. Where necessary to specifically distinguish between ubiquitin and ubiquitin-like modifiers, the attachment of e.g. NEDD8 or ISG15 to target proteins is termed NEDDylation or ISGylation, respectively. Thereby, target proteins are NEDDylated or ISGylated, respectively.

A "ubiquitinated peptide" may also refer to the product that results from the digestion of a ubiquitinated polypeptide with a hydrolyzing agent, such as LysC, i.e., a peptide containing at least one ubiquitin remnant. In the preferred embodiment of the invention, a binding partner is used that specifically recognizes and binds to a ubiquitin remnant peptide but does not cross react with other peptides having the same amino acid sequence but which lack the ubiquitin remnant. The preferred binding partner is an anti-ubiquitin remnant peptide antibody or fragment thereof.

The term "antibody" as used herein, refers to immunoglobulin molecules and immunologically active portions of immunoglobulin molecules, i.e., molecules that contain an antigen binding site that specifically binds to an antigen. As such, the term antibody encompasses not only whole antibody molecules, but also antibody multimers and antibody fragments, as well as variants (including derivatives) of antibodies, antibody multimers and antibody fragments.

EXAMPLE

Both polyclonal and monoclonal antibodies capable of recognizing the remnant of ubiquitin left from ubiquitinated proteins after digestion with the protease LysC were generated. These antibodies were generated as follows.

Exemplified Workflow

Monoclonal Antibody Generation, Peptide Purification Column Setup:

A peptide (ESTLHLVLRLRGGC (SEQ ID NO 7), comprising the ubiquitin remnant ESTLHLVLRLRGG (SEQ ID NO 1)) is conjugated with KLH and used as immunogen. BALB/c mice were immunized with the conjugated peptide, and mice showing immune response were used for cell fusion and hybridoma production. Antibodies derived from a hybridoma cell line can be purified e.g. on Protein G covalently bound to resin material (e.g. sepharose or agarose) or other affinity purification materials, including the epitope peptide bound to support resin. Antibodies can be eluted from the support material or cross-linked to it. Eluted and/or purified antibodies can be covalently coupled to other resin materials, e.g. tosyl-activated matrices.

Sample Preparation and Peptide Digest:

Lysate from cells is digested with the protease LysC. In case of ubiquitinated proteins present in the cell lysate, this generates "branched" peptides, comprising of the ubiquitin remnant ESTLHLVLRLRGG (SEQ ID NO 1) covalently bound to the epsilon amino group of a lysine residue in the ubiquitinated peptide sequence. This modified lysine residue does not function as a cleavage site for hydrolytic enzymes such as LysC, leaving the ubiquitin remnant (SEQ ID NO 1) intact and attached to the epsilon amino group of the such modified lysine residue which itself is part of a LysC cleavage product. Using the described antibody (e.g. bound to a resin support), peptides containing the ubiquitin remnant ESTLHLVLRLRGG (SEQ ID NO 1) can be selectively enriched from other, not such modified peptides present in the lysate.

Two variations for detection and identification of ubiquitinated peptides are exemplified:

(1) Indirect Detection Method

Enriched ubiquitin remnant ESTLHLVLRLRGG (SEQ ID NO 1) containing LysC peptides are further processed by proteolytical digest with e.g. Trypsin. Trypsin cleaves C-terminal to lysine or arginine residues. The ubiquitin remnant ESTLHLVLRLRGG (SEQ ID NO 1) will thereby be cleaved, leaving a diglycine modification (GG) at the epsilon amino group of the modified Lysine residue.

After subjecting these peptides to a peptide analyser (e.g. a mass spectrometer), peptides carrying the diglycine ubiquitin remnant can be identified by database search or de novo sequencing, thereby allowing identification of the ubiquitination site in the protein and the protein itself, from which the modified peptide was derived.

(2) Direct Detection Method

Enriched ubiquitin remnant ESTLHLVLRLRGG (SEQ ID NO 1) containing LysC peptides are directly subjected to a peptide analyser (e.g. a mass spectrometer), and peptides carrying the ubiquitin remnant ESTLHLVLRLRGG (SEQ ID NO 1) can be identified by e.g. database search and de novo sequencing or targeted approaches, thereby allowing to identify the ubiquitination site in the protein from which the modified peptide was derived.

The first method (1) is easier to integrate in e.g. mass spectrometry based proteomics workflows, as diglycine signatures can be easily searched for in database searching approaches. The second method (2) requires in depth analysis of fragment ion data to identify spectra, because fragment ions derived from the ubiquitin remnant ESTLHLVLRLRGG (SEQ ID NO 1) are also present and increase the complexity of fragment ion data.

The invention claimed is:

1. A method of detecting a ubiquitinated site in a sample protein or a mixture of sample proteins that comprises
   (i) cleaving a sample protein or a mixture of sample proteins with a protease comprising LysC that cleaves ubiquitin to form a mixture of cleavage peptides, wherein the protease comprises LysC that cleaves ubiquitin also cleaves protein(s) in the sample or the mixture of sample protein;
   (ii) contacting the cleavage peptides with an antibody that specifically binds to an epitope having the sequence ESTLHLVLRLRGG (SEQ ID NO 1), said antibody being able to specifically distinguish between proteins and peptides that are ubiquitinated and proteins and peptides that are modified by ubiquitin-like modifiers;
   (iii) analysing the peptide(s) that bind to the antibody thereby detecting and identifying an ubiquitinated site in the test sample protein of the mixture of the sample proteins;
   (iv) sequencing the cleavage peptide to which the antibody binds to thereby determine the amino acids sequence of the cleavage peptide; and
   (v) identifying the ubiquitinated site in the cleavage peptide,
      wherein the sequencing/identification is performed by a method comprising mass spectrometry.

2. The method of claim 1, wherein the cleavage peptide is further hydrolysed prior to sequencing and identification by a second protease, wherein the second protease for hydrolyzing is trypsin.

3. The method of claim 1, wherein the sample is a body fluid, tissue sample, cell lysate, fractionated cellular material, cellular extract, cell culture supernatant, or cultured cells.

4. A method of detecting an ubiquitinated site in sample protein or a mixture of sample proteins that comprises
   (i) cleaving a sample protein or a mixture of sample proteins with a protease comprising LysN that cleaves ubiquitin to form a mixture of cleavage peptides, wherein the protease comprises LysN that cleaves ubiquitin also cleaves protein(s) in the sample or the mixture of sample protein;
   (ii) contacting the cleavage peptides with an antibody that specifically binds to an epitope having the sequence KESTLHLVLRLRGG (SEQ ID NO 6), said antibody being able to specifically distinguish between proteins and peptides that are ubiquitinated and proteins and peptides that are modified by ubiquitin-like modifiers;
   (iii) analysing the peptide(s) that bind to the antibody thereby detecting and identifying an ubiquitinated site in the test sample protein or the mixture of test sample proteins;
   (iv) sequencing the cleavage peptide to which the antibody binds to thereby determine the amino acids sequence of the cleavage peptide; and
   (v) identifying the ubiquitinated site in the cleavage peptide, wherein the sequencing/identification is performed by a method comprising mass spectrometry.

5. The method of claim 4, wherein the cleavage peptide is further hydrolysed prior to sequencing and identification by a second protease, wherein the second protease for hydrolyzing is trypsin.

\* \* \* \* \*